United States Patent
Papania-Davis et al.

(10) Patent No.: US 12,049,024 B2
(45) Date of Patent: Jul. 30, 2024

(54) CONCRETE PREPARATION AND RECIPE OPTIMIZATION

(71) Applicant: X Development LLC, Mountain View, CA (US)

(72) Inventors: Antonio Raymond Papania-Davis, Oakland, CA (US); Neil David Treat, San Jose, CA (US); Kathy Feng Liu, Sandy, UT (US); Scott Glover, Cambridge, MA (US)

(73) Assignee: X Development LLC, Mountain View, CA (US)

( * ) Notice: Subject to any disclaimer, the term of this patent is extended or adjusted under 35 U.S.C. 154(b) by 567 days.

(21) Appl. No.: 17/159,496

(22) Filed: Jan. 27, 2021

(65) Prior Publication Data
US 2022/0234249 A1 Jul. 28, 2022

(51) Int. Cl.
*B28C 7/02* (2006.01)
*B28C 7/04* (2006.01)
(Continued)

(52) U.S. Cl.
CPC ............ *B28C 7/024* (2013.01); *B28C 7/0418* (2013.01); *G01N 15/02* (2013.01); *G01N 33/383* (2013.01); *G16C 20/10* (2019.02); *G16C 20/20* (2019.02); *G16C 60/00* (2019.02); *G01N 2015/1029* (2024.01); *G01N 2015/103* (2024.01)

(58) Field of Classification Search
CPC ... B28C 7/024; B28C 7/0418; C04B 40/0032; G01N 15/02
See application file for complete search history.

(56) References Cited

U.S. PATENT DOCUMENTS

| 5,527,387 A | 6/1996 | Andersen et al. |
| 7,736,432 B2 | 6/2010 | Buesing et al. |
| (Continued) | | |

FOREIGN PATENT DOCUMENTS

| CN | 208576041 | 3/2019 |
| JP | 2003291132 | 10/2003 |
| (Continued) | | |

OTHER PUBLICATIONS

International Preliminary Report on Patentability in International Appln. No. PCT/US2022/012432, dated Aug. 10, 2023, 12 pages.

(Continued)

*Primary Examiner* — Elizabeth Insler
(74) *Attorney, Agent, or Firm* — Fish & Richardson P.C.

(57) ABSTRACT

Methods, systems, and apparatus, including computer programs encoded on computer storage media, for preparing a concrete mixture. One of the methods includes controlling an ingredient metering system to measure and add a plurality of ingredients to a concrete mixture, measuring characteristics of at least one ingredient of the ingredients using a particle analyzer, determining an estimated rheometry measurement of for the concrete mixture, obtaining an actual rheometry measurement of the concrete mixture, and selectively controlling the ingredient metering system to add one or more additional ingredients to the concrete mixture based on a comparison of the estimated rheometry measurement with the actual rheometry measurement.

19 Claims, 4 Drawing Sheets

(51) Int. Cl.
    *G01N 15/02*    (2024.01)
    *G01N 33/38*    (2006.01)
    *G16C 20/10*    (2019.01)
    *G16C 20/20*    (2019.01)
    *G16C 60/00*    (2019.01)
    *G01N 15/10*    (2006.01)

(56) References Cited

U.S. PATENT DOCUMENTS

| | | |
|---|---|---|
| 9,707,513 B2 | 7/2017 | Constantz et al. |
| 9,714,406 B2 | 7/2017 | Constantz et al. |
| 9,789,629 B2 | 10/2017 | Kochler et al. |
| 9,993,799 B2 | 6/2018 | Constantz et al. |
| 10,197,747 B2 | 2/2019 | Constantz et al. |
| 10,203,434 B2 | 2/2019 | Constantz et al. |
| 10,287,439 B2 | 5/2019 | Constantz et al. |
| 10,322,371 B2 | 6/2019 | Constantz et al. |
| 10,711,236 B2 | 7/2020 | Constantz et al. |
| 10,766,015 B2 | 9/2020 | Constantz et al. |
| 10,898,854 B2 | 1/2021 | Constantz et al. |
| 10,960,350 B2 | 3/2021 | Constantz et al. |
| 11,181,700 B2 | 11/2021 | Constantz et al. |
| 11,262,488 B2 | 3/2022 | Constantz et al. |
| 11,344,861 B2 | 5/2022 | Constantz et al. |
| 2008/0009976 A1 | 1/2008 | Andersen et al. |
| 2010/0197818 A1 | 8/2010 | Sweat |
| 2019/0242802 A1 | 8/2019 | Beaupre |
| 2020/0171704 A1 | 6/2020 | Davis et al. |
| 2020/0370001 A1 | 11/2020 | Constantz et al. |
| 2020/0402619 A1 * | 12/2020 | Tregger ................ B28C 5/422 |
| 2021/0162340 A1 | 6/2021 | Constantz et al. |
| 2021/0236989 A1 | 8/2021 | Constantz et al. |
| 2021/0356680 A1 | 11/2021 | Constantz et al. |
| 2022/0214477 A1 | 7/2022 | Constantz et al. |
| 2022/0250028 A1 | 8/2022 | Constantz et al. |

FOREIGN PATENT DOCUMENTS

| | | | |
|---|---|---|---|
| KR | 101936218 | 1/2019 | |
| WO | WO 2015/057729 | 4/2015 | |
| WO | WO-2015057729 A3 * | 7/2015 | ......... B01D 46/2418 |
| WO | WO 2019/210389 | 11/2019 | |
| WO | WO 2022/010399 | 1/2022 | |

OTHER PUBLICATIONS

International Search Report and Written Opinion in International Appln. No. PCT/US2022/012432, dated Apr. 22, 2022, 30 pages.
Design and Control of Concrete, 14th ed., Kosmatka et al., Feb. 2002, Chapter 9, 29 pages.
GiatecScientific.com [online], "Concrete Mix Design Just Got Easier," Dec. 8, 2020, retrieved on Jan. 29, 2021, retrieved from URL <https://www.giatecscientific.com/education/concrete-mix-design-just-got-easier/>, 19 pages.
Guidelines for Reviewing Concrete Mix Designs In Accordance with the 2010 CBC, Structural Engineers Association of Norther California, Jul. 2013, 60 pages.
Hydronix.com [online], "Moisture Measurement in Concrete Production," retrieved on Jan. 29, 2021, retrieved from URL <https://www.hydronix.com/applications/moisture_in_concrete.php>, 1 page.

* cited by examiner

CONCRETE PREPARATION AND RECIPE OPTIMIZATION

BACKGROUND

Concrete is the second most consumed substance (by mass) on our planet and is responsible for 7-8% of global $CO_2$ emissions. Concrete's material properties are inconsistent due to the large variation in ingredient material (e.g., aggregates) and processing. This material inconsistency requires large safety margins for a given performance level and results in material overuse. Advances in concrete preparation that can optimize the use of locally available materials to maximize concrete performance while minimizing cost with both traditional and non-traditional concrete ingredients are desirable.

SUMMARY

In general, this disclosure relates to a process and system for preparing and mixing concrete to achieve target post-curing characteristics. In particular, concrete ingredients are characterized as they are measured for addition to a concrete mixture. Rheometry measurements are performed on the initial concrete mixture. Rheometry measurements of the concrete mixture with the ingredients added can be estimated based on the measured characteristics of the ingredients. The rheometry measurements are used to predict characteristics of the concrete after curing. The actual rheometry measurements of the concrete mixture can be obtained and compared with the estimated rheometry to determine whether to add additional ingredients. The system can determine, based on the rheometry measurements, whether the concrete mixture is likely to achieve a desired set of post-curing characteristics. If not, the initial mixture is adjusted through an iterative process until the rheometry measurements indicate that the concrete mixture is likely to achieve the desired post-curing characteristics.

During the iterative adjustment process, portions of concrete ingredients are incrementally added to the initial concrete mixture while changes in the rheometry measurements are monitored. Additional portions of ingredients are added until the rheometry measurements indicate that the concrete mixture is likely to achieve the desired post-curing characteristics. Such post-curing characteristics can include, but are not limited to, compressive strength, tensile/flexural strength, flowability, toughness, cure time, cure profile, finish, density (wet & dry), thermal insulation, shrinkage, and slump.

In some examples, ingredients are characterized by a particle analyzer as they are measured and added to the concrete mixture. For example, ingredients, such as aggregates, can be monitored by a particle analyzer as they are dispensed from a hopper. The particle analyzer employs various sensors to detect characteristics such as particle size, particle size distribution, particle shape, and/or particle surface area. The rheometry measurements of the concrete mixture with the ingredients added can be estimated based on the measured characteristics of the ingredient. The estimated rheometry measurements can be compared with the actual rheometry measurements of the mixture to determine whether additional ingredients need to be added to achieve desired structural properties for the concrete.

Post-curing characteristics can be determined from rheometry measurements by, e.g., using multi-dimensional lookup tables relating experimentally obtained post-curing characteristics to mixtures with known rheological properties, by applying theoretical and analytical particle packing model-based Bayesian optimization algorithms to the rheometry measurements, or a combination thereof.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
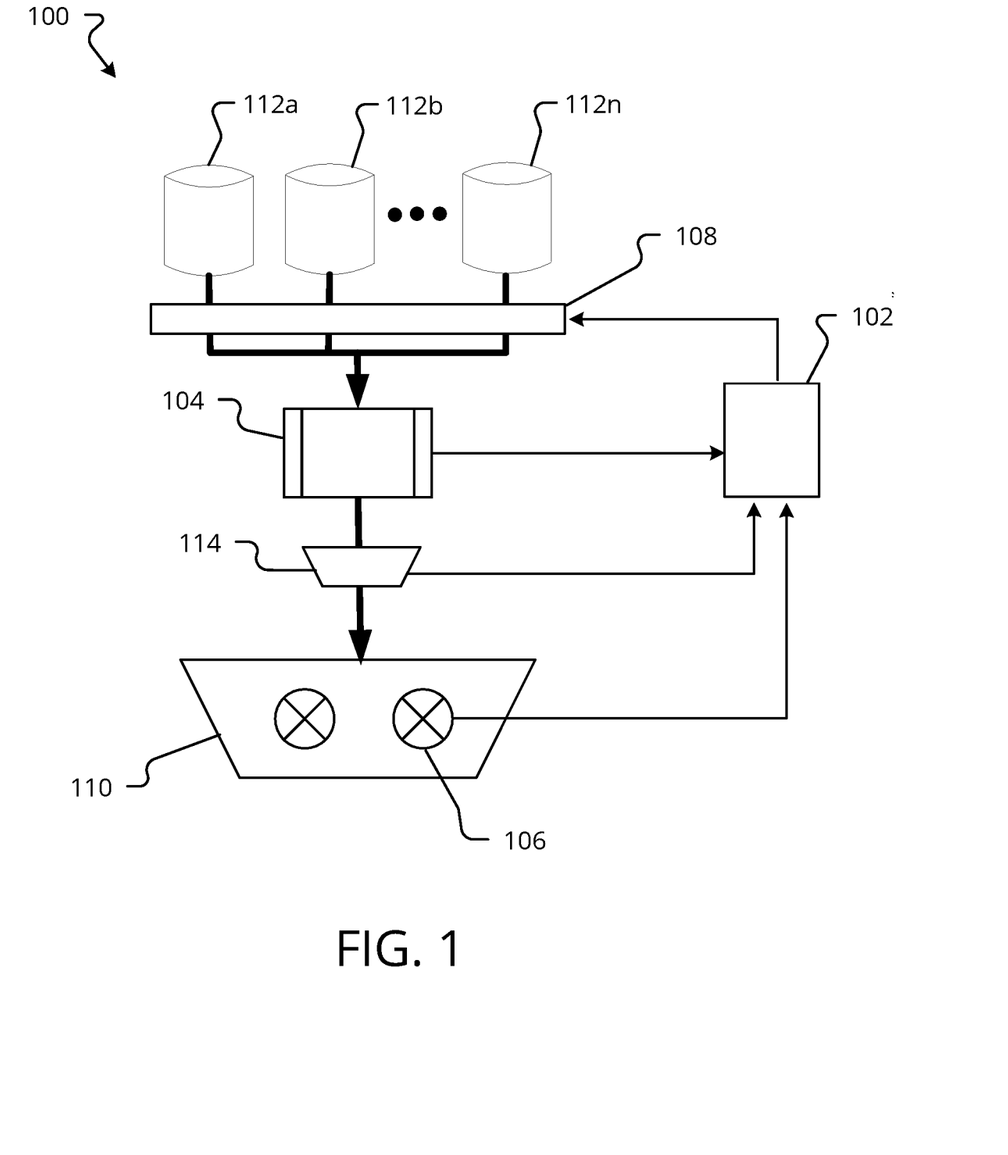
FIG. 1 depicts an exemplary concrete preparation system.

FIG. 1 depicts an exemplary concrete preparation system 100. Concrete preparation system 100. In operation, concrete preparation system 100 measures characteristics of the raw ingredients of a concrete mixture. Concrete preparation system 100 can adaptively adjust the proportion of the raw ingredients added to the concrete mixture based on the measured characteristics to more accurately achieve desired structural properties in the final cured concrete. The operation of the system 100 is described in more detail below in reference to FIGS. 2 and 3.

Concrete preparation system 100 includes a control system 102. The control system 102 receives input from particle analyzing system 104 and concrete mix sensors 106. The control system 102 can control the operations of one or more ingredient metering systems 108 based on analyses of data obtained from one or both of the particle analyzing system 110 and concrete mix sensors 106.

Concrete preparation system 100 includes raw ingredient storage bays or hoppers 112*a*-112*n*. The ingredient metering system 108 conveys the raw ingredients from the storage bays 112*a*-112*n* to a mixing vessel 110. For example, the ingredient metering system 108 can include a series of conveyors and augers to transfer raw ingredients from the storage bays 112*a*-112*n* into the mixing vessel 110. The concrete preparation system 100 differs from traditional concrete plants in that the raw ingredients are passed through the particle analyzing system 104 prior to delivery to the mixing vessel 110.

In some implementations, the ingredient metering system 108 may include a metering hopper 114 between the particle analyzing system 104 and the mixing vessel 110. The metering hopper 114 may be used to collect and measure (e.g., weigh) a raw ingredient as it passes through the particle analyzing system 104. For example, the weight of the ingredient measured by metering hopper 114 can be passed to the control system 100 permitting the control system to monitor the weight of the ingredient being measured in real-time. The control system 102 may then be able to make in-situ adjustments to how much of the ingredient to add to the concrete mixture based on real-time particle analysis of the ingredient from the particle analyzing system 104. In some implementations, concrete preparation system 100 can be retro-fit to a traditional ready-mix concrete plant. For example, adding the concrete preparation system 100 to a ready-mix plant may allow the ready-mix plant to more precisely tailor concrete mixes for specific applications and job sites.

The particle analyzing system 104 can include various different sensors configured to measure various characteristics of concrete ingredients. For example, the sensors used by the particle analyzing system 104 can include, but are not limited to, optical sensors (e.g., visible light cameras, infrared cameras, dynamic optical microscopy sensors) and mechanical sensors (e.g., sieves, sedigraphs, impact hammer, electrodynamic vibrator). The measurement data is used by the control system 102 to determine characteristics of the ingredients of the concrete mixture. For example, ingredient characteristics can include, but are not limited to, particle sizes, particle shapes, surface areas, and particle sphericity.

The sensors of the particle analyzing system 104 are arranged to obtain measurement data of concrete ingredients as the ingredients are added to a concrete mixture. For example, in some implementations optical sensors can be arranged in an array along a conveyor or a chute used to convey the raw ingredients to the mixing vessel 110. The optical sensors can transmit images of the ingredients to the control system 102, which (as explained in more detail below) can use image processing algorithms to identify particle shapes and sizes.

Some implementations may include a series of sieves to separate particles of an ingredient by size. In such implementations, the optical sensors can be positioned proximate to each sieve to capture images of the particles passing through the sieve. The images can then be used, for example, to determine an approximate count of each size range of particles exiting each sieve. In such implementations, the separated particles may be recombined before being added to the mixing vessel 110.

The concrete mix sensors 106 provide rheometry measurements of the concrete mixture to the control system 102. For example, the concrete mix sensors 106 can measure various attributes of the concrete mixture that can be used to estimate or compute rheumatic properties of the concrete mixture in real-time. The concrete mix sensors 106 can include, but are not limited to, viscosity sensors, rheometers, temperature sensors, moisture sensors, ultrasonic sensors (e.g., ultrasonic pulse velocity sensors), electrical property sensors (e.g., electrodes, electrical resistance probes), electromagnetic sensors (e.g., short-pulse radar), or other sensors (e.g., geophone, accelerometer). The concrete mix sensors 106 can include, but are not limited to, hydrophobicity, moisture content, XRD spectra, XRF spectra, static yield stress, acoustic impedance, p-wave speed, dynamic yield stress, static modulus of elasticity, Young's modulus, bulk modulus, shear modulus, dynamic modulus of elasticity (DME), Poisson's ratio, density, resonance frequency, nuclear magnetic resonance (NMR), dielectric constant, electric resistivity, polarization potential, and capacitance.

For example, viscosity, moisture, and temperature sensors can be installed in the mixing vessel 110. These sensors can be used to measure rheologic properties of the concrete mixture such as changes in the viscosity of the mixture over time and at different moisture content levels and temperatures. As described in more detail below, the control system 102 can use the rheometry measurements to determine whether and how much additional ingredients should be added to the concrete mixture to obtain desired concrete properties.

Figure 2:
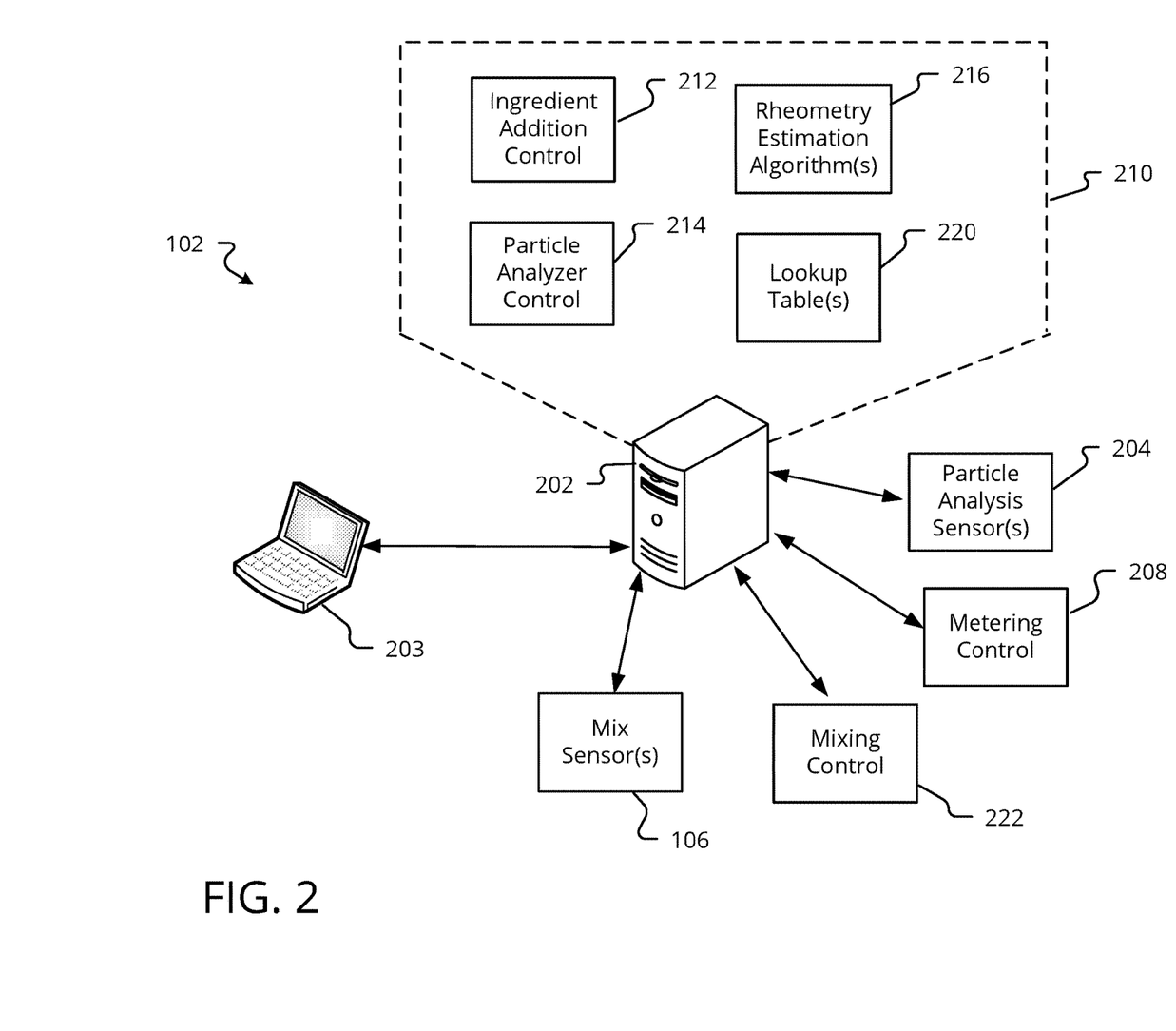
FIG. 2 depicts a block diagram of an exemplary control system for the concrete preparation system of FIG. 1.

FIG. 2 is a block diagram of an exemplary control system 102 for the concrete preparation system 100. The system 102 includes a computing system 202 in communication with the concrete mix sensors 106, particle analysis sensors 204 of the particle analyzing system 104, a metering control system 208 which can control operations of the ingredient metering system 108. Computing system 202 is configured to control various aspects of the concrete preparation process. For example, computing system 202 can store and execute one or more computer instruction sets to control the execution of aspects of the concrete preparation processes described herein. Computing system 202 can include a system of one or more computing devices. The computing devices can be, e.g., a system of one more servers. For example, a first server can be configured to receive and process data from the concrete mix sensors 106 and the particle analysis sensors 204. Another server can be configured to interface with the metering control system 208 and issue control commands based on analysis results from the first server.

In some implementations, the computing system 202 can be operated or controlled from a user computing device 203. User computing device 203 can be a computing device, e.g., desktop computer, laptop computer, tablet computer, or other portable or stationary computing device.

Briefly, computing system 202 can control the overall concrete preparation system 100 to prepare concrete mixtures. The computing system 202 can use the particle analysis sensors 204 to characterize concrete ingredients as they are added to a concrete mixture. The computing system 202 obtains rheometry measurements from the mix sensors 106 as the concrete mixture is mixed in the mixing vessel 110. The system compares the rheometry measurements with estimated rheometry measurements to determine, e.g., whether the concrete mixture will meet desired post-curing mechanical properties or whether additional ingredients should be added.

In some implementations, computing system 202 can include a set of operations modules 210 for controlling different aspects of a concrete additive manufacturing process. The operation modules 210 can be provided as one or more computer executable software modules, hardware modules, or a combination thereof. For example, one or more of the operation modules 210 can be implemented as blocks of software code with instructions that cause one or more processors of the computing system 202 to execute operations described herein. In addition or alternatively, one or more of the operations modules can be implemented in electronic circuitry such as, e.g., programmable logic circuits, field programmable logic arrays (FPGA), or application specific integrated circuits (ASIC). The operation modules 210 can include an ingredient addition controller 212, a particle analyzer controller 214, rheometry estimation algorithms 216, rheometry measurement algorithms 218, and one or more lookup tables 220.

Ingredient addition controller 212 interfaces with the metering control system 208 to control the addition of ingredients to the concrete mixing vessel 110. For example, the ingredient addition controller 212 can issue commands from the computing system 202 to the metering control system 208 to control the addition of ingredients to the concrete mixture in the mixing vessel 110.

Particle analyzer control 214 interfaces with the particle analysis sensors 204 of the particle analyzing system 104. Particle analyzer controller 214 receives and buffers data from the particle analysis sensors 204. The particle analyzer controller 214 can process the sensor data to determine particle characteristics of each analyzed ingredient. For example, as discussed in more detail below, the particle analyzer controller 214 can execute data analysis algorithms to interpret the sensor data and determine particle characteristics including, but not limited to, particle size distributions, particle shape distributions, and particle surface area distributions.

The control system can employ rheometry estimation algorithms 216 to estimate the rheometry parameters of a given concrete mixture based on the particle characteristics of the ingredients. For example, the rheometry estimation algorithms 216 can employ lookup tables 220 to determine estimated rheometry measurements. The computing system can include a lookup table 220 that correlates concrete particle characteristics to experimentally determined rheometry parameters. In some implementations, the rheometry estimation algorithms 216 include algorithms that estimate particle packing efficiencies from the particle parameters and a lookup table 220 that correlates particle packing efficiencies with experimentally determined rheometry parameters. The computing system 202 can then compare the estimated particle packing efficiencies to the data in the lookup table 220 to estimate the rheometry parameters of the concrete mixture.

In some implementations, rheometry estimation algorithms 216 include a packing efficiency model to determine a packing efficiency of the ingredients based on the particle characteristics. The model can be a theoretical and analytical particle packing model-based Bayesian optimization algorithm—or other machine learning model—to determine a packing efficiency of the particles and estimate rheometry parameters of the mixture.

In some implementations, the rheometry estimation algorithms 216 can include a machine learning model to estimate particle packing efficiency and/or rheometry parameters for a concrete mixture from measured particle characteristics. For example, the machine learning model can include a model that has been trained on experimental data to receive particle characteristics of concrete ingredients as input, and to generate a predicted output, e.g., an estimate of the particle packing efficiency, an estimate of rheometry parameters for a concrete mixture, or both. In some implementations, the machine learning model is a deep learning model that employs multiple layers of models to generate an output for a received input. A deep neural network is a deep machine learning model that includes an output layer and one or more hidden layers that each apply a non-linear transformation to a received input to generate an output. In some cases, the neural network may be a recurrent neural network. A recurrent neural network is a neural network that receives an input sequence and generates an output sequence from the input sequence. In particular, a recurrent neural network uses some or all of the internal state of the network after processing a previous input in the input sequence to generate an output from the current input in the input sequence. In some other implementations, the machine learning model is a convolutional neural network. In some implementations, the machine learning model is an ensemble of models that may include all or a subset of the architectures described above.

In some implementations, the machine learning model can be a feedforward autoencoder neural network. For example, the machine learning model can be a three-layer autoencoder neural network. The machine learning model may include an input layer, a hidden layer, and an output layer. In some implementations, the neural network has no recurrent connections between layers. Each layer of the neural network may be fully connected to the next, there may be no pruning between the layers. The neural network may include an ADAM optimizer, or any other multi-dimensional optimizer, for training the network and computing updated layer weights. In some implementations, the neural network may apply a mathematical transformation, such as a convolutional transformation, to input data prior to feeding the input data to the network.

In some implementations, the machine learning model can be a supervised model. For example, for each input provided to the model during training, the machine learning model can be instructed as to what the correct output should be. The machine learning model can use batch training, training on a subset of examples before each adjustment, instead of the entire available set of examples. This may improve the efficiency of training the model and may improve the generalizability of the model. The machine learning model may use folded cross-validation. For example, some fraction (the "fold") of the data available for training can be left out of training and used in a later testing phase to confirm how well the model generalizes. In some implementations, the machine learning model may be an unsupervised model. For example, the model may adjust itself based on mathematical distances between examples rather than based on feedback on its performance.

A machine learning model can be trained to estimate rheometry parameters for concrete mixtures based on measured characteristics of the ingredients to the mixture. In some examples, the machine learning model can be trained on experimentally determined data relating known characteristics of concrete ingredients to experimentally determined rheometry parameters.

The computing system 202 can store one or more lookup tables 220 that correlate different measured parameters to experimentally determined characteristics of a concrete mixture or post-curing concrete. For example, the lookup tables 220 can include one or more of: a table correlating desired post-curing concrete characteristics to concrete mixture rheometry parameters, a table correlating ingredient characteristics to particle packing efficiencies, and a table correlating ingredient characteristics to mixture remoter parameters. Each lookup table can be a multi-dimensional data structure containing measurable concrete parameters, concrete mixture parameters, or ingredient characteristics to experimentally determined parameters.

Figure 3:
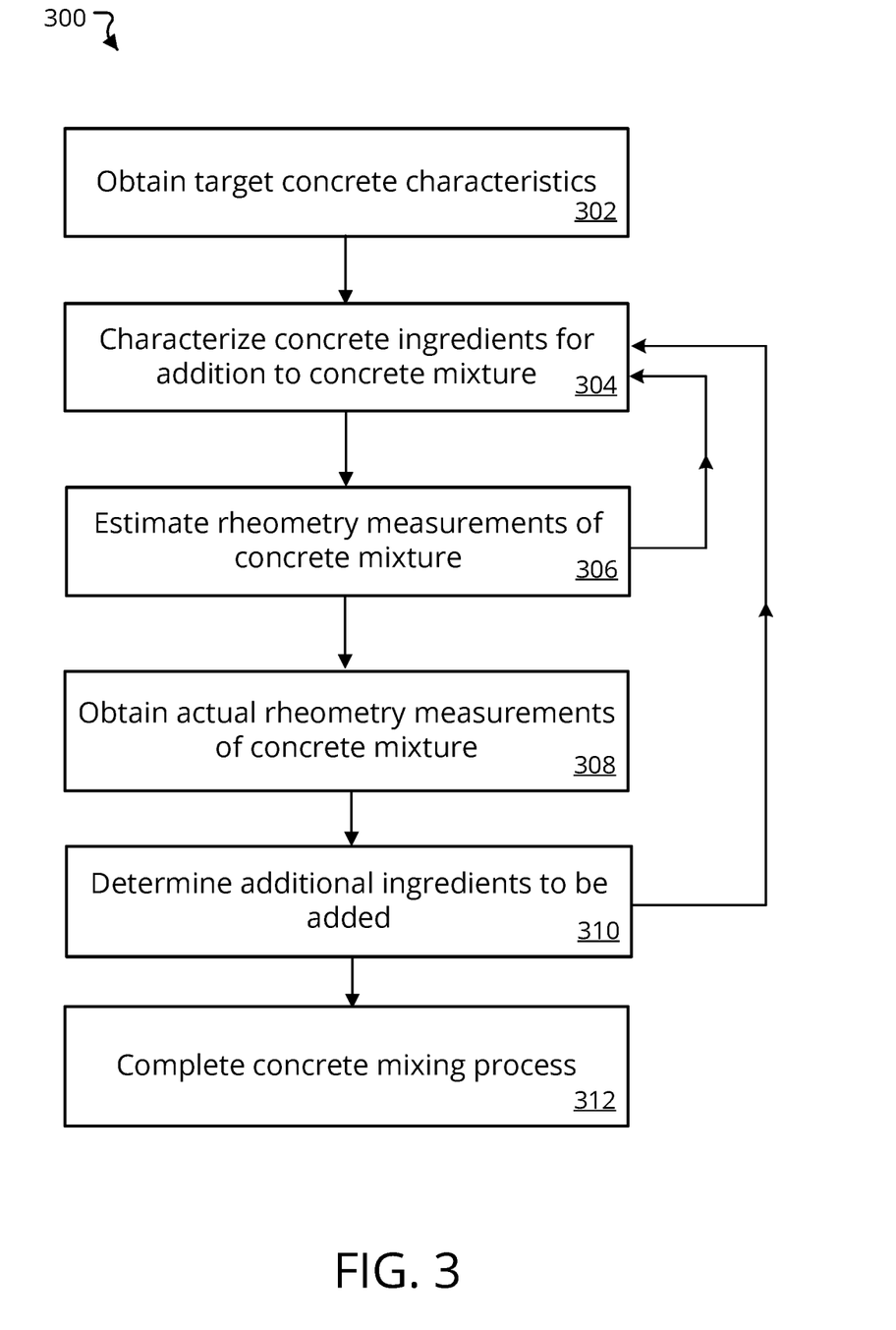
FIG. 3 depicts a flow diagram that illustrates an example process for operating the concrete preparation system of FIG. 1.

FIG. 3 is a flow diagram that illustrates a process 300 for controlling operation of a concrete preparation system 100. The process 300 can be performed by one or more computing devices. For example, as discussed above, the process 300 may be performed by computing system 202 of FIG. 2. For convenience, operations of process 300 is described as being performed by a control system. However, as noted above, some or all of the operations may be performed by various operation modules of an additive manufacturing control system.

The control system obtains target concrete characteristics (302). For example, the control system can obtain target post-curing concrete characteristics from a user. The post-curing characteristics can include, but are not limited to, compressive strength, tensile strength, and thermal expansion/contraction properties. The control system can, e.g., receive the target characteristics as input provided by the user.

In some implementations, the control system can estimate a target rheology for the concrete mixture that would produce the target post-curing characteristics. For example, rheometry estimation algorithms can be used to estimate target rheology measurements for the concrete mixture from the target post-curing characteristics. The target post-curing characteristics can be compared against entries in a lookup table of experimentally obtained post-curing characteristics from various different concrete mixtures. The lookup table can be a multi-dimensional table that associates various concrete mix rheometry parameters with post-curing characteristics. The system can compare the input target characteristics to entries in the lookup table 220 to identify target rheometry parameters for the concrete mixture.

The control system characterizes concrete ingredients for addition to the concrete mixture (304). For example, the control system can obtain measurement data from a particle analyzing system as the ingredients (e.g., sand, aggregate, etc.) are conveyed to a concrete mixing vessel. As discussed above, the control system can receive data from various particle sensors of the particle analyzing system. The control system can analyze the sensor data to characterize one or more of the ingredients as they are conveyed to the concrete mixing vessel. For example, the control system can use image analysis algorithms to detect general shapes and sizes of aggregate particles as they are conveyed through a chute or on a conveyor belt.

The control system can estimate a distribution of the various shapes and sizes of the aggregate particles. For example, the control system can characterize an ingredient (e.g., an aggregate) by developing a histogram of the particle size distribution within the aggregate and a histogram of particle shape distribution within the aggregate. The control system can employ the image analysis algorithm to obtain a rough count of aggregate particles within each of a series of size ranges (e.g., >2 mm, 2 mm-3 mm, 3 mm-4 mm, 4 mm-5 mm, etc.). In some implementations, the control system can similarly employ the image analysis algorithm to obtain a rough count of aggregate particles with various shapes or degrees of sphericity. In some implementations, the computing system can characterize the particles by both size and shape distribution.

In some implementations, the control system selects a "base" recipe for the concrete. The "base" recipe may be a set of initial ingredients for a concrete mixture that will approximate the target rheometry parameters. For example, the control system can select a "base" recipe based on the target rheometry for the concrete mixture and/or additional user input. For example, the control system can use a second lookup table that associates rheometry parameters with base ingredients for a concrete mixture to select a "base" recipe. The control system can then control the ingredient metering system to begin conveying the ingredients of the base recipe into the concrete mixing vessel. The control system can then analyze the ingredients as they are added to the mixing vessel as described above.

The control system estimates rheometry measurements of the concrete mixture (306). For example, the control system can use the particle characteristics of the ingredients to estimate rheometry parameters of the concrete mixture. The control system can use a packing efficiency model to determine a packing efficiency of the ingredients based on the particle characteristics. In some implementations, the control system can use a theoretical and analytical particle packing model-based Bayesian optimization algorithm—or other machine learning model—to determine a packing efficiency of the particles and estimate rheometry parameters of the mixture.

In some implementations, the control system can use a lookup table of experimental data to correlate measured particle characteristics (e.g., size/shape distributions) to experimentally determined rheometry parameters. For example, the computing system can compare the measured particle characteristics to entries in the lookup table and estimate the rheometry parameters of the concrete mixture based on correlating entries of experimentally determined rheometry parameters in the lookup table. In some examples, the control system may interpolate between entries in the lookup table or extrapolate the table data when the measured particle characteristics do not precisely match with a table entry.

In some implementations, the control system includes a machine learning model that is trained using the experimentally determined correlations between particle size characteristics and rheometry parameters. In such implementations, the control system can provide the particle characteristics for the concrete ingredients to the trained machine learning model as input data vectors. The machine learning model may correlate the input particle characteristics with expected rheometry parameters for the resulting concrete mixture and output the expected rheometry parameters.

In some implementations, the estimated rheometry parameters can be compared with the target rheometry parameters. If the estimated rheometry parameters differ by a threshold amount from the target rheometry parameters, the control system can control the ingredient metering system to add additional ingredients to the concrete mixture, e.g., to preemptively adjust the rheometry of the mixture. For example, the control system can determine whether the actual characteristics of the particles of the ingredients differed from characteristics that would have been expected in order to achieve the target rheometry parameters. The control system may compare an expected packing efficiency of the ingredient particles with the packing efficiency that was determined based on the measured particle characteristics. The control system can then identify one or more additional ingredients (which may be different from those originally added) which will alter the packing efficiency of ingredients in the concrete mixture in a manner that will shift the estimated rheometry parameters to more closely conform with the target rheometry parameters. The control system may select different ingredients to add based on which parameters deviate from the target parameters, the magnitude of the difference, the direction of the difference (e.g., whether the estimated parameters are greater or less than the target paramours), or a combination thereof. For example, the control system may estimate a viscosity for a concrete mixture based on measured particle characteristics that is lower than a target viscosity. The control system may determine from the measured particle characteristics that the distribution sizes of the individual particles of the aggregate that was added to the concrete mixture were larger than expected. For instance, a 20 mm aggregate may have been selected as part of the "base" recipe. However, the average size of the aggregate may exceed 20 mm by a threshold value (e.g., 5 mm) that caused the packing efficiency to be reduced, thus resulting in an expected viscosity lower than the target viscosity. As a result, the control system can select an aggregate that will increase the packing efficiency and the viscosity of the concrete mixture, e.g., a smaller sized aggregate, for addition to the mixture. The process 300 would then return to step 304, in which the control system controls the ingredient metering system to add and characterize the selected aggregate. The process 300 may repeat steps 304 and 306 until the estimated rheometry parameters are within the threshold amount of the target rheometry parameters.

The control system obtains actual rheometry measurements of the concrete mixture (308). For example, the control system can receive measurement data from the mix sensors indicating rheometry parameters of the concrete mixture while it is being mixed in the mixing vessel. In some implementations, the control system can control the operation of the mixing equipment within the mixing vessel to supplement the sensors. For example, the control system can control the speed of the mixing equipment to obtain viscosity and/or shear measurements of the concrete mixture.

The control system determines whether additional ingredients need to be added and, selectively, adds the additional ingredients (310). For example, the control system can compare the measured rheometry parameters with the target rheometry parameters to determine how closely the concrete mixture conforms to the target parameters. As discussed above, the target rheometry parameters for the mixture can serve as a proxy for the post-curing structural characteristics of the concrete (e.g., based on experimental data). If the measured rheometry parameters differ by a threshold amount from the target rheometry parameters, the control system can control the ingredient metering system to add additional ingredients to the concrete mixture to adjust the rheometry of the mixture. The control system can then identify one or more additional ingredients (which may be different from those originally added) which will alter the rheometry of the concrete mixture in a manner that will shift the measured rheometry parameters to more closely conform with the target rheometry parameters. The control system may select different ingredients to add based on which parameters deviate from the target parameters, the magnitude of the difference, the direction of the difference (e.g., whether the estimated parameters are greater or less than the target paramours), or a combination thereof. For example, the control system may measure a viscosity for the concrete mixture that is higher than a target viscosity. As a result, the control system can select an aggregate that will decrease the packing efficiency and the viscosity of the concrete mixture, e.g., a smaller sized aggregate, for addition to the mixture. Alternatively, if the magnitude of the difference between the measured viscosity and the target viscosity is small, the control system can select to add some additional water to reduce the viscosity. The process 300 would then return to step 304, in which the control system controls the ingredient metering system to add and characterize the selected ingredient. The process 300 may repeat steps 304-310 until the measured rheometry parameters are within the threshold amount of the target rheometry parameters. Once the target rheometry parameters are achieved (e.g., within threshold values), then the concrete mixing process is complete (312).

Figure 4:
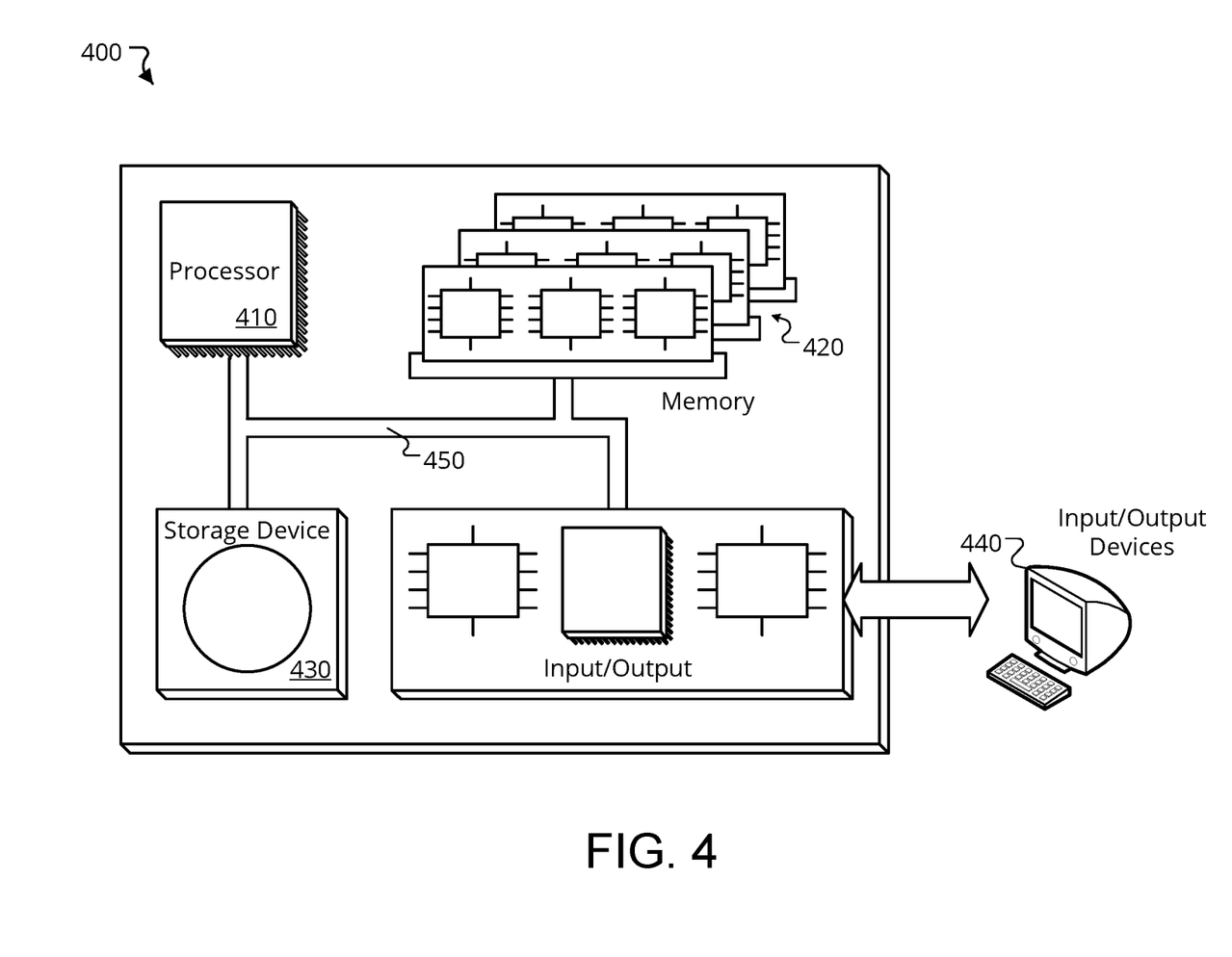
FIG. 4 depicts a schematic diagram of a computer system that may be applied to any of the computer-implemented methods and other techniques described herein.

FIG. 4 is a schematic diagram of a computer system 400. The system 400 can be used to carry out the operations described in association with any of the computer-implemented methods described previously, according to some implementations. In some implementations, computing systems and devices and the functional operations described in this specification can be implemented in digital electronic circuitry, in tangibly-embodied computer software or firmware, in computer hardware, including the structures disclosed in this specification (e.g., system 400) and their structural equivalents, or in combinations of one or more of them. The system 400 is intended to include various forms of digital computers, such as laptops, desktops, workstations, personal digital assistants, servers, blade servers, mainframes, and other appropriate computers, including vehicles installed on base units or pod units of modular vehicles. The system 400 can also include mobile devices, such as personal digital assistants, cellular telephones, smartphones, and other similar computing devices. Additionally, the system can include portable storage media, such as, Universal Serial Bus (USB) flash drives. For example, the USB flash drives may store operating systems and other applications. The USB flash drives can include input/output components, such as a wireless transducer or USB connector that may be inserted into a USB port of another computing device.

The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. The processor may be designed using any of a number of architectures. For example, the processor 410 may be a CISC (Complex Instruction Set Computers) processor, a RISC (Reduced Instruction Set Computer) processor, or a MISC (Minimal Instruction Set Computer) processor.

In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the system 400. In one implementation, the storage device 430 is a computer-readable medium. In various different implementations, the storage device 430 may be a floppy disk device, a hard disk device, an optical disk device, or a tape device.

The input/output device 440 provides input/output operations for the system 400. In one implementation, the input/output device 440 includes a keyboard and/or pointing device. In another implementation, the input/output device 440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touch-screen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

As used herein, the term "ready mix" refers to concrete that is batched for delivery from a central plant instead of being mixed on a job site. Typically, a batch of ready mix is tailor-made according to the specifics of a particular construction project and delivered in a plastic condition, usually in cylindrical trucks often referred to as "concrete mixers".

As used herein, the term "real-time" refers to transmitting or processing data without intentional delay given the processing limitations of a system, the time required to accurately obtain data, and the rate of change of the data. Although there may be some actual delays, the delays are generally imperceptible to a user.

Although the disclosed inventive concepts include those defined in the attached claims, it should be understood that the inventive concepts can also be defined in accordance with the following embodiments.

In addition to the embodiments of the attached claims and the embodiments described above, the following numbered embodiments are also innovative.

Embodiment 1 is a method of preparing a concrete mixture, the method comprising: controlling an ingredient metering system to measure and add a plurality of ingredients to a concrete mixture; measuring, using a particle analyzer, characteristics of at least one ingredient of the ingredients; determining, based on the measured characteristics, an estimated rheometry measurement of for the concrete mixture; obtaining an actual rheometry measurement of the concrete mixture; and selectively controlling the ingredient metering system to add one or more additional ingredients to the concrete mixture based on a comparison of the estimated rheometry measurement with the actual rheometry measurement.

Embodiment 1 may provide one or more of the following technical advantages or effects: adaptively adjusting the proportion of the raw ingredients added to a concrete mixture based on measured characteristics of the ingredients, and may more accurately achieve desired structural properties in the final cured concrete.

Embodiment 2 is the method of embodiment 1, wherein the characteristics of the at least one ingredient comprises one or more of a particle size distribution, a particle shape distribution, or particle sphericity.

Embodiment 3 is the method of any one of embodiments 1 or 2, wherein determining an estimated rheometry measurement of the concrete mixture comprises determining, based on the characteristics, a particle packing efficiency for the at least one ingredient, and determining the estimated rheometry measurement based at least in part on the particle packing efficiency.

Embodiment 4 is the method of embodiment 3, wherein determining the estimated rheometry measurement based at least in part on the particle packing efficiency comprises comparing the particle packing efficiency to a multi-dimensional lookup table that associates particle packing efficiencies to experimentally determined expected rheometry measurements.

Embodiment 5 is the method of any one of embodiments 3 or 4, wherein determining the particle packing efficiency comprises applying characteristics as input to a Bayesian optimization algorithm.

Embodiment 6 is the method of any one of embodiments 1 through 5, further comprising: iteratively adjusting the concrete mixture until a stop condition is achieved, wherein each iteration comprises: obtaining rheometry measurements of the concrete mixture; determining, based on the rheometry measurements, whether the concrete mixture satisfies the stop condition; in response to the rheometry measurements not satisfying the stop condition: determining additional portions for one or more of the ingredients to be added to the concrete mixture in order to meet a set of target concrete characteristics, and controlling the ingredient metering system to measure and add the additional portions to the concrete mixture; and in response to determining that the concrete mixture satisfies the stop condition, ceasing the iteratively adjusting the concrete mixture.

Embodiment 7 is the method of embodiment 6, wherein the stop condition is the set of target concrete characteristics.

Embodiment 8 is the method of any one of embodiments 6 or 7, wherein determining whether the concrete mixture satisfies the stop condition comprises determining whether the rheometry measurements indicate that the concrete mixture is likely to achieve at least one of the set of target concrete characteristics within a threshold value.

Embodiment 9 is the method of embodiment 8, wherein determining whether the rheometry measurements indicate that the concrete mixture is likely to achieve at least one of the set of target concrete characteristics comprises: determining target rheometry parameters based on a multi-dimensional lookup table associating experimentally obtained post-curing characteristics to concrete mixtures with known rheological properties; and comparing the rheometry measurements to the target rheometry parameters.

Embodiment 10 is a concrete mixing system comprising: a mixing vessel; one or more raw material hoppers; an ingredient metering system configured to measure and add ingredients from the one or more hoppers to the mixing vessel; a particle analyzing system configured to measure characteristics of the ingredients; and a control system configured to perform operations comprising: controlling the ingredient metering system to measure and add a plurality of ingredients to a concrete mixture; measuring, using the particle analyzer, characteristics of at least one ingredient of the ingredients; determining, based on the measured characteristics, an estimated rheometry measurement of for the concrete mixture; obtaining an actual rheometry measurement of the concrete mixture; and selectively controlling the ingredient metering system to add one or more additional ingredients to the concrete mixture based on a comparison of the estimated rheometry measurement with the actual rheometry measurement.

Embodiment 10 may provide one or more of the following technical advantages or effects: adaptively adjusting the proportion of the raw ingredients added to a concrete mixture based on measured characteristics of the ingredients, and may more accurately achieve desired structural properties in the final cured concrete.

Embodiment 11 is the system of embodiment 10, wherein the characteristics of the at least one ingredient comprises one or more of a particle size distribution, a particle shape distribution, or particle sphericity.

Embodiment 12 is the system of embodiment 11, wherein determining an estimated rheometry measurement of the concrete mixture comprises determining, based on the characteristics, a particle packing efficiency for the at least one ingredient, and determining the estimated rheometry measurement based at least in part on the particle packing efficiency.

Embodiment 13 is the system of embodiment 12, wherein determining the estimated rheometry measurement based at least in part on the particle packing efficiency comprises comparing the particle packing efficiency to a multi-dimensional lookup table that associates particle packing efficiencies to experimentally determined expected rheometry measurements.

Embodiment 14 is the system of any one of embodiments 12 or 13, wherein determining the particle packing efficiency comprises applying characteristics as input to a Bayesian optimization algorithm.

Embodiment 15 is the system of any one of embodiments 10 through 14, wherein the operations further comprise: iteratively adjusting the concrete mixture until a stop condition is achieved, wherein each iteration comprises: obtaining rheometry measurements of the concrete mixture; determining, based on the rheometry measurements, whether the concrete mixture satisfies the stop condition; in response to the rheometry measurements not satisfying the stop condition: determining additional portions for one or more of the ingredients to be added to the concrete mixture in order to meet a set of target concrete characteristics, and controlling the ingredient metering system to measure and add the additional portions to the concrete mixture; and in response to determining that the concrete mixture satisfies the stop condition, ceasing the iteratively adjusting the concrete mixture.

Embodiment 16 is the system of embodiment 15, wherein the stop condition is the set of target concrete characteristics.

Embodiment 17 is the system of any one of embodiments 15 and 16, wherein determining whether the concrete mixture satisfies the stop condition comprises determining whether the rheometry measurements indicate that the concrete mixture is likely to achieve at least one of the set of target concrete characteristics within a threshold value.

Embodiment 18 is the system of embodiment 17, wherein determining whether the rheometry measurements indicate that the concrete mixture is likely to achieve at least one of the set of target concrete characteristics comprises: determining target rheometry parameters based on a multi-dimensional lookup table associating experimentally obtained post-curing characteristics to concrete mixtures with known rheological properties; and comparing the rheometry measurements to the target rheometry parameters.

Embodiment 19 is the system of embodiment any one of embodiments 10 through 18, wherein the particle analyzing system comprises one or more sensors selected from the group consisting of optical sensors or mechanical sensors.

Embodiment 20 is a system comprising one or more computers and one or more storage devices storing instructions that are operable, when executed by the one or more computers, to cause the one or more computers to perform the method of any one of claims 1 to 9.

Embodiment 21 is a computer program carrier encoded with a computer program, the program comprising instructions that are operable, when executed by data processing apparatus, to cause the data processing apparatus to perform the method of any one of claims 1 to 9.

While this specification contains many specific implementation details, these should not be construed as limitations on the scope of what is being claimed, which is defined by the claims themselves, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claim may be directed to a subcombination or variation of a subcombination.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A method of preparing a concrete mixture, the method comprising:
    controlling an ingredient metering system to measure and add a plurality of ingredients to a concrete mixture;
    measuring, using a particle analyzer, characteristics of at least one ingredient of the ingredients, the characteristics comprising shapes of particles of the at least one ingredient;
    determining, based on the measured characteristics, an estimated rheometry measurement of the concrete mixture by applying the measured characteristics of the at least one ingredient as input to a machine learning model configured to generate estimated rheometry parameters of the mixture as output, wherein the input comprises input data vectors that represent the measured characteristics of the at least one ingredient, and wherein the estimated rheometry measurement comprises one or more output estimated rheometry parameters;
    obtaining an actual rheometry measurement of the concrete mixture; and
    selectively controlling the ingredient metering system to add one or more additional ingredients to the concrete mixture based on a comparison of the estimated rheometry measurement with the actual rheometry measurement.

2. The method of claim 1, wherein the characteristics of the at least one ingredient comprises one or more of a particle size distribution, or particle sphericity.

3. The method of claim 2, wherein determining an estimated rheometry measurement of the concrete mixture comprises determining, based on the characteristics, a particle packing efficiency for the at least one ingredient, and determining the estimated rheometry measurement based at least in part on the particle packing efficiency.

4. The method of claim 3, wherein determining the particle packing efficiency comprises applying characteristics as input to a second machine learning model, wherein the second machine learning model is a Bayesian optimization algorithm.

5. The method of claim 1, further comprising:
    iteratively adjusting the concrete mixture until a stop condition is achieved, wherein each iteration comprises:
        obtaining rheometry measurements of the concrete mixture;
        determining, based on the rheometry measurements, whether the concrete mixture satisfies the stop condition;
        in response to the rheometry measurements not satisfying the stop condition:
            determining additional portions for one or more of the ingredients to be added to the concrete mixture in order to meet a set of target concrete characteristics, and
            controlling the ingredient metering system to measure and add the additional portions to the concrete mixture; and
        in response to determining that the concrete mixture satisfies the stop condition, ceasing the iteratively adjusting the concrete mixture.

6. The method of claim 5, wherein the stop condition is the set of target concrete characteristics.

7. The method of claim 5, wherein determining whether the concrete mixture satisfies the stop condition comprises determining whether the rheometry measurements indicate that the concrete mixture is likely to achieve at least one of the set of target concrete characteristics within a threshold value.

8. The method of claim 7, wherein determining whether the rheometry measurements indicate that the concrete mixture is likely to achieve at least one of the set of target concrete characteristics comprises:
    determining target rheometry parameters based on a multi-dimensional lookup table associating experimentally obtained post-curing characteristics to concrete mixtures with known rheological properties; and
    comparing the rheometry measurements to the target rheometry parameters.

9. The method of claim 1, wherein selectively controlling the ingredient metering system comprises determining, based on the comparison, a type of ingredient and an amount of the ingredient to add to the concrete mixture.

10. The method of claim 1, wherein the machine learning model is trained using one or more experimentally determined correlations between one or more particle size characteristics and rheometry parameters of at least one ingredient of the ingredients.

11. A concrete mixing system comprising:
    a mixing vessel;
    one or more raw material hoppers;

an ingredient metering system configured to measure and add ingredients from the one or more hoppers to the mixing vessel;
a particle analyzing system configured to measure characteristics of the ingredients; and
a control system configured to perform operations comprising:
controlling the ingredient metering system to measure and add a plurality of ingredients to a concrete mixture;
measuring, using the particle analyzer, characteristics of at least one ingredient of the ingredients, the characteristics comprising shapes of particles of the at least one ingredient;
determining, based on the measured characteristics, an estimated rheometry measurement of the concrete mixture by applying the measured characteristics of the at least one ingredient as input to a machine learning model configured to generate estimated rheometry parameters of the mixture as output, wherein the input comprises input data vectors that represent the measured characteristics of the at least one ingredient, and wherein the estimated rheometry measurement comprises one or more output estimated rheometry parameters;
obtaining an actual rheometry measurement of the concrete mixture; and
selectively controlling the ingredient metering system to add one or more additional ingredients to the concrete mixture based on a comparison of the estimated rheometry measurement with the actual rheometry measurement.

12. The system of claim 11, wherein the characteristics of the at least one ingredient comprises one or more of a particle size distribution, or particle sphericity,
wherein determining an estimated rheometry measurement of the concrete mixture comprises determining, based on the characteristics, a particle packing efficiency for the at least one ingredient, and determining the estimated rheometry measurement based at least in part on the particle packing efficiency.

13. The system of claim 12, wherein determining the estimated rheometry measurement based at least in part on the particle packing efficiency comprises comparing the particle packing efficiency to a multi-dimensional lookup table that associates particle packing efficiencies to experimentally determined expected rheometry measurements.

14. The system of claim 12, wherein determining the particle packing efficiency comprises applying characteristics as input to a second machine learning model, wherein the second machine learning model is a Bayesian optimization algorithm.

15. The system of claim 11, the operations further comprising:
iteratively adjusting the concrete mixture until a stop condition is achieved, wherein each iteration comprises:
obtaining rheometry measurements of the concrete mixture;
determining, based on the rheometry measurements, whether the concrete mixture satisfies the stop condition;
in response to the rheometry measurements not satisfying the stop condition:
determining additional portions for one or more of the ingredients to be added to the concrete mixture in order to meet a set of target concrete characteristics, and
controlling the ingredient metering system to measure and add the additional portions to the concrete mixture; and
in response to determining that the concrete mixture satisfies the stop condition, ceasing the iteratively adjusting the concrete mixture.

16. The system of claim 15, wherein the stop condition is the set of target concrete characteristics.

17. The system of claim 15, wherein determining whether the concrete mixture satisfies the stop condition comprises determining whether the rheometry measurements indicate that the concrete mixture is likely to achieve at least one of the set of target concrete characteristics within a threshold value.

18. The system of claim 17, wherein determining whether the rheometry measurements indicate that the concrete mixture is likely to achieve at least one of the set of target concrete characteristics comprises:
determining target rheometry parameters based on a multi-dimensional lookup table associating experimentally obtained post-curing characteristics to concrete mixtures with known rheological properties; and
comparing the rheometry measurements to the target rheometry parameters.

19. The system of claim 11, wherein the particle analyzing system comprises one or more sensors selected from the group consisting of optical sensors or mechanical sensors.

* * * * *